United States Patent
Newman-Tancredi et al.

(10) Patent No.: US 11,974,992 B2
(45) Date of Patent: May 7, 2024

(54) USE OF SEROTONIN 5-HT1A RECEPTOR AGONISTS TO TREAT DISEASES ASSOCIATED WITH SUDDEN UNEXPECTED DEATH IN EPILEPSY

(71) Applicants: Neurolixis, Labruguiere (FR); The Regents of the University of California, Oakland, CA (US)

(72) Inventors: Adrian Newman-Tancredi, Castres (FR); Mark A. Varney, Park Ridge, CA (US); Khaleelurrahman Abdulrazak, Riverside, CA (US); Xin Tao, Riverside, CA (US)

(73) Assignees: Neurolixis, Labruguiere (FR); The Regents of the University of California, Oakland, CA (US)

( * ) Notice: Subject to any disclaimer, the term of this patent is extended or adjusted under 35 U.S.C. 154(b) by 0 days.

(21) Appl. No.: 17/586,477

(22) Filed: Jan. 27, 2022

(65) Prior Publication Data

US 2023/0233539 A1    Jul. 27, 2023

Related U.S. Application Data

(60) Provisional application No. 63/303,372, filed on Jan. 26, 2022.

(51) Int. Cl.
*A61K 31/4427* (2006.01)
*A61K 31/451* (2006.01)
*A61K 31/506* (2006.01)

(52) U.S. Cl.
CPC ........ *A61K 31/4427* (2013.01); *A61K 31/451* (2013.01); *A61K 31/506* (2013.01)

(58) Field of Classification Search
CPC . A61K 31/4427; A61K 31/451; A61K 31/506
USPC ....................................................... 514/256
See application file for complete search history.

(56) References Cited

U.S. PATENT DOCUMENTS

2018/0092864 A1* 4/2018 Martin .................. A61P 25/08

FOREIGN PATENT DOCUMENTS

WO    2016138138 A1    9/2016
WO    WO-2019216919 A1 * 11/2019 ........... A61K 31/137

OTHER PUBLICATIONS

Petrucci et al., Exp Neurol. Mar. 2020 ; 325: 113145. doi:10.1016/j.expneurol.2019.113145. Serotonin and sudden unexpected death in epilepsy (Year: 2020).*
Protic et al. Current Pediatric Reviews, 2019, 15, 251-258, "New Targeted Treatments for Fragile X Syndrome" (Year: 2019).*
Armstrong et al. ACS Pharmacol. Transl. Sci. 2020, 3, 509-523, (Year: 2020).*
Newman-Tancredi , Neuropsychiatry 2011, 1(2), 149-164. https://doi.org/10.2217/npy.11.12. Biased agonism at serotonin 5-HT1A receptors: Preferential postsynaptic activity for improved therapy of CNS disorders. (Year: 2011).*
Richerson et al. Epilepsia. Jan. 2011 ; 52(Suppl 1): 28-38. "The serotonin axis: Shared mechanisms in seizures, depression and SUDEP". (Year: 2011).*
Telias, Current Pharmaceutical Design, 2019, 25, 4394-4404, "Pharmacological Treatments for Fragile X Syndrome Based on Synaptic Dysfunction" (Year: 2019).*
Canal et al., "An Orally Active Phenylaminotetralin-Chemotype Serotonin 5-HT7 and 5-HT1A Receptor Partial Agonist That Corrects Motor Stereotypy in Mouse Models", ACS Chemical Neuroscience, 2015, pp. 1259-1270, vol. 6, No. 7.
Sniecikowska et al., "Novel Aryloxyethyl Derivatives of 1-(1-Benzoylpiperidin-4-yl)methanamine as the Extracellular Regulated Kinases 1/2 (ERK1/2) Phosphorylation-Preferring Serotonin 5-HT1A Receptor-Biased Agonists with Robust Antidepressant-like Activity", Journal of Medicinal Chemistry, 2019, pp. 2750-2771, vol. 62, No. 5.

* cited by examiner

*Primary Examiner* — Jared Barsky
*Assistant Examiner* — Liyuan Mou
(74) *Attorney, Agent, or Firm* — Thompson Coburn LLP; Steven M. Ritchey

(57) ABSTRACT

The present application concerns the treatment and prevention of diseases associated with an increased risk of sudden unexpected death in epilepsy, such as Fragile X syndrome, by administering a selective 5-HT1A receptor agonist.

3 Claims, 2 Drawing Sheets

USE OF SEROTONIN 5-HT1A RECEPTOR AGONISTS TO TREAT DISEASES ASSOCIATED WITH SUDDEN UNEXPECTED DEATH IN EPILEPSY

CROSS-REFERENCE TO RELATED APPLICATIONS

This application claims the benefit of U.S. Provisional Application No. 63/303,372, filed on Jan. 26, 2022, which is incorporated herein by reference in its entirety.

The present invention concerns the field of therapeutic treatment of diseases associated with Sudden Unexpected Death in Epilepsy (SUDEP), such as Fragile X Syndrome (FXS).

Seizure or epileptic seizure is a period of symptoms due to abnormally excessive or synchronous neuronal activity in the brain. Fatal complications of epilepsy may lead to SUDEP, which is defined as the sudden and unexpected, non-traumatic and non-drowning death of a person with epilepsy, without a toxicological or anatomical cause of death. Not all seizures lead to SUDEP. It has been hypothesized that certain seizure types or seizures occurring in certain patients may be associated with an increased risk of SUDEP.

Seizures associated with SUDEP typically occur in certain diseases.

Among them is Fragile X syndrome (FXS), a rare genetic disorder caused by mutation of the FMR1 gene, causing a loss of function of the FMRP protein which is important for brain development. Subjects with FXS suffer from a range of symptoms, including sensory hypersensitivity and a propensity to epileptic seizures.

Transgenic mice lacking FMRP function (i.e., FMR1 knock-out mice) are an animal model of FXS and are prone to audiogenic seizures (i.e., seizures induced by loud noise) which, if prolonged, result in death.

There are also mutations in the SCN1A, SCN1B, SCN8A, SCN2A, GNB5, KCNA1, CDKL5 and DEPDC5 genes which can lead to SUDEP.

Other diseases associated with seizures include Dravet syndrome, Guillain-Barré syndrome, Ohtahara syndrome, Angelman syndrome, myoclonic astatic epilepsy (MAE), and Lennox-Gastaut syndrome.

It is therefore desirable to provide novel candidates for treating diseases associated with SUDEP. It is also desirable to provide novel candidates for treating SUDEP.

In terms of brain neurobiology, the nexus between seizures and serotonin (5-hydroxytryptamine: 5-HT) receptors has been established. However, the role of specific sub-types of serotonin receptors, including $5\text{-HT}_{1A}$, is under debate.

Indeed, previous reports are conflicting concerning the effects of $5\text{-HT}_{1A}$ receptor agonists (i.e., ligands that activate $5\text{-HT}_{1A}$ receptors) on seizures in wild-type rodents (i.e., not suffering from a genetic abnormality that would confer susceptibility to epilepsy): some reports show increases, whereas other reports show decreases:

Studies reported contradictory results on the activity of 8-OH-DPAT, a dual $5\text{-HT}_{1A}/5\text{-HT}_7$ receptor agonist on seizures (Yang et al Neurosci Bull. 2014 June; 30(3):401-8. doi: 10.1007/s12264-013-1396-x. Epub 2014 Jan. 15. PMID: 24429728; Fujii et al Yakubutsu Seishin Kodo. 1991 February; 11(1):29-35. PMID: 1831945). Moreover, when 8-OH-DPAT was tested in FMR1 knock-out mice on electrophysiological and cellular tests, its effects were found to be mediated by $5\text{-HT}_7$ and not $5\text{-HT}_{1A}$ receptors (Costa et al. Biol Psychiatry. 2012 Dec. 1; 72(11):924-33. doi: 10.1016/j.biopsych.2012.06.008. Epub 2012 Jul. 18. PMID: 22817866).

Obniska et al. reported $5\text{-HT}_{1A}/5\text{-HT}_7$ compounds with anticonvulsant activity, but it is unclear if these compounds are agonists or antagonists (Pharmacol Rep. 2005 May-June; 57(3):336-44.PMID: 15985716). Moreover, the authors also reported that other $5\text{-HT}_{1A}/5\text{-HT}_7$ ligands showed no correlation between anticonvulsant activity and their serotonergic properties (Pharmacol Rep. 2005 May-June; 57(3):336-44. PMID: 15985716).

Lately, some authors reported that vilazodone, which acts as a $5\text{-HT}_{1A}$ receptor agonist, induces seizures in humans (McKean et al. Pharmacotherapy. 2015 March; 35(3):e6-8. doi: 10.1002/phar.1549. PMID: 25809181).

There is therefore no clear consensus on the role of $5\text{-HT}_{1A}$ receptors in seizures, and more particularly on the possible influence of selective $5\text{-HT}_{1A}$ receptors agonists on seizures associated with SUDEP.

WO2016/138138 also discloses the treatment of epilepsy with 5-HT receptor agonists, binding to $5\text{-HT}_{2A}$ and $5\text{-HT}_{2B}$ receptors but without significant binding to $5\text{-HT}_{1A}$ receptors. In any case, there is no mention of selective $5\text{-HT}_{1A}$ agonists in this patent.

Overall, although serotonin may be believed to be important in the pathophysiology of seizures in diseases such as FXS, no established role has been demonstrated for $5\text{-HT}_{1A}$ receptors, and the effects of selective $5\text{-HT}_{1A}$ receptor agonists have not been investigated on pre-clinical models of FXS or of other diseases associated with SUDEP.

NLX-101 (also known as F-15599) has been disclosed in WO03/106449. It is a compound which highly selectively targets serotonin $5\text{-HT}_{1A}$ receptors and has been tested in preclinical and clinical studies. It has a distinctive property, known as 'biased agonism', whereby it directs $5\text{-HT}_{1A}$ receptors to preferentially activate specific intracellular signaling pathways, notably ERK1/2 phosphorylation, as opposed to other signaling pathways. The biased agonist properties of NLX-101 are associated with activation of specific brain regions (Lladó-Pelfort et al J Pharmacol. 2010 August; 160(8):1929-40. doi: 10.1111/j.1476-5381.2010.00738.x.PMID: 20649591).

Levitt et al J. Appli. Physiol. 115:1626-1633, 2013 report that NLX-101 improves the respiratory abnormalities in a mouse model of the Rett syndrome. Nevertheless, the possible effects of NLX-101 on SUDEP have not been investigated.

The inventors have now found that NLX-101 unexpectedly reduces audiogenic seizures in FMR1 knock-out mice, and have established that selective $5\text{-HT}_{1A}$ receptor agonists may therefore be useful for treating FXS and other diseases associated with SUDEP.

Therefore, the present invention provides for a method of treatment or prevention of a disease associated with SUDEP chosen from the group consisting in seizures, Fragile X syndrome, Dravet syndrome, Guillain-Barré syndrome, Ohtahara syndrome, Angelman syndrome, myoclonic astatic epilepsy (MAE), Lennox-Gastaut syndrome and diseases associated with the FMR1, SCN1A, SCN1B, SCN8A, SCN2A, GNB5, KCNA1, CDKL5 or DEPDC5 gene dysfunction, comprising administering a therapeutically effective amount of a selective $5\text{-HT}_{1A}$ receptor agonist in a patient suffering from such a disease.

The present invention also provides for a method of treatment or prevention of seizures comprising administering a therapeutically effective amount of a selective 5-HT$_{1A}$ receptor agonist in a patient suffering from a disease where SUDEP occurs.

According to an embodiment, said disease where SUDEP occurs include Fragile X syndrome, Dravet syndrome, Guillain-Barré syndrome, Ohtahara syndrome, Angelman syndrome, Rett syndrome, myoclonic astatic epilepsy (MAE), Lennox-Gastaut syndrome and diseases associated with the FMR1, SCN1A, SCN1B, SCN8A, SCN2A, GNB5, KCNA1, CDKL5 or DEPDC5 gene dysfunction More preferably, said diseases are chosen from Fragile X syndrome, Dravet syndrome, Guillain-Barré syndrome and Ohtahara syndrome.

In particular, the inventors found that NLX-101 did not exhibit any anti-seizure activity in wild-type (i.e., non-transgenic) mice, using two widely used models of epileptic seizures induced by corneal electrical stimulation. In contrast, when tested in the audiogenic tonic-clonic seizure model in FMR1 knock-out mice over a similar dose-range, NLX-101 potently and efficaciously reduced seizures and protected over 75 percent of the mice from death.

The absence of effect of NLX-101 on corneal electrically induced seizures in wild-type mice suggests a general lack of anti-seizure activity for the compound. Consequently, the anti-seizure activity of NLX-101 on audiogenic seizures in transgenic FMR1 mice was unexpected and suggests an activity of selective 5-HT$_{1A}$ receptor agonists on certain seizure types, particularly those associated with SUDEP.

The capacity of NLX-101 to reduce seizures and death in FMR1 knock-out mice may arise from the very selective agonist properties of NLX-101 at 5-HT$_{1A}$ receptors. Moreover, its biased agonist activity for activation of ERK1/2 phosphorylation may contribute to its anti-seizure and anti-SUDEP properties.

As used herein, "associated with SUDEP" refers to a disease that may lead to an increased risk of SUDEP when compared with the general patient population, typically at least 10% more preferably at least 20%, more preferably at least 30% more SUDEP than in the general patient population. Such increased risk may correspond to certain seizure types and/or they may occur in certain patient populations.

As used herein, the term "diseases" refers to health disorders, and encompasses both the established medical conditions having defined reasons, as well as syndromes (ie) a collection of symptoms which may not necessarily have an identifiable cause.

The treatment of such diseases includes the removal of the causes and/or the attenuation of the symptoms.

According to an embodiment, the 5-HT$_{1A}$ receptor agonist is a selective biased 5-HT$_{1A}$ receptor agonist.

According to a preferred embodiment, the selective 5-HT$_{1A}$ receptor agonist is selected from the group consisting in compounds of formula (I):

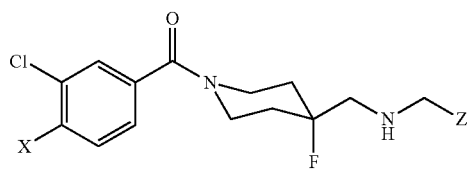

Where
X represents a halogen atom;
Z represents a —(CH$_2$—Y)$_n$—Ar group where:
n is 0 or 1;
Y is chosen from —CH$_2$—, —NH—, —S— or —O—; and
Ar represents a 5 to 10 membered aryl or heteroaryl ring optionally substituted by one or more C1-C6 alkyl groups;
Or one of the pharmaceutically acceptable salts or esters thereof.

As used herein, "Alkyl" means an aliphatic hydrocarbon group which may be straight or branched having about 1 to about 6 carbon atoms in the chain, optionally substituted with one or more substituents which may be the same or different, and include halo, hydroxy, cyano, amino, alkoxy. Exemplary alkyl groups include methyl, ethyl, n-propyl, i-propyl.

"Aryl" means an aromatic monocyclic or bicyclic ring system of 5 to about 10 carbon atoms, preferably of about 6 to about 10 carbon atoms. Exemplary aryl groups include phenyl or naphthyl.

"Heteroaryl" means an aromatic monocyclic or bicyclic ring system of about 5 to about 10 atoms, preferably about 5 to about 10 carbon atoms, in which at one or more of the atoms in the ring system is/are hetero element(s) other than carbon, for example nitrogen, oxygen or sulfur. Preferred ring sizes of rings of the ring system include about 5 to about 6 ring atoms. The designation of the aza, oxa or thia as a prefix before heteroaryl defines that at least a nitrogen, oxygen or sulfur atom is present respectively as a ring atom. A nitrogen atom of an heteroaryl may be a basic nitrogen atom and may also be optionally oxidized to the corresponding N-oxide. Exemplary heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl. Preferred heteroaryl groups include pyrazinyl, pyridyl, pyrimidinyl.

According to a preferred embodiment, the compound of formula (I) is chosen from compounds (IA) and (II) below which are closely related and which also exhibit similar biased agonist properties for activation of ERK1/2 phosphorylation:

NLX-101 of formula (IA):

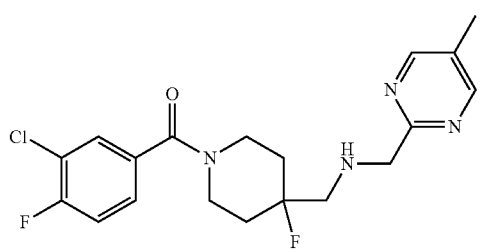

Or one of the pharmaceutically acceptable salts or esters thereof; and compounds of formula (II):

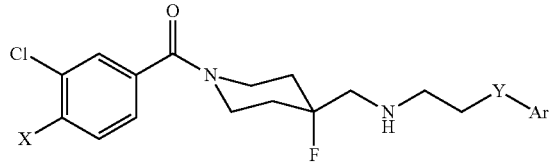

(II)

Where

X is chosen from F and Cl;

Y is chosen from —CH$_2$—, —NH—, —S—, or —O—; and

Ar is chosen from phenyl and N-containing 6-membered monocyclic heteroaryl groups, optionally substituted by one or more C1-C6 alkyl groups;

Or one of the pharmaceutically acceptable salts or esters thereof.

According to an embodiment, in Formula (II):

X is chosen from F and Cl; and

The group

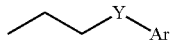

is chosen from the group consisting in:

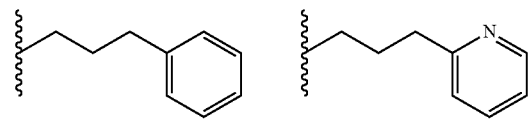

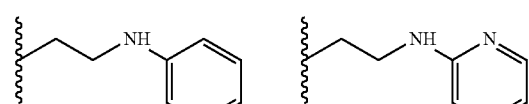

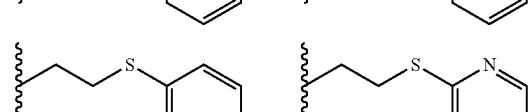

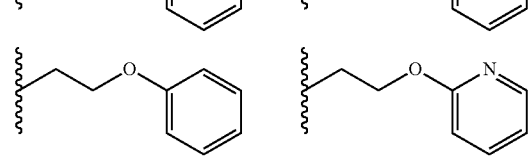

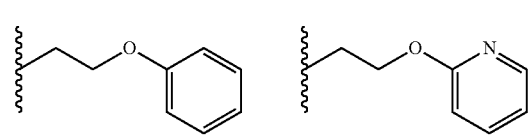

According to a further embodiment, in Formula (II):
X=F;
Y=—O—; and
Ar is chosen from the group consisting of:

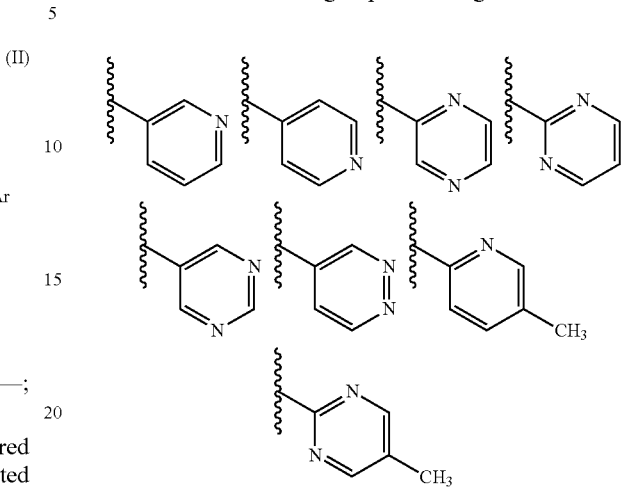

According to a particular embodiment, compounds of formula (II) can be chosen from:

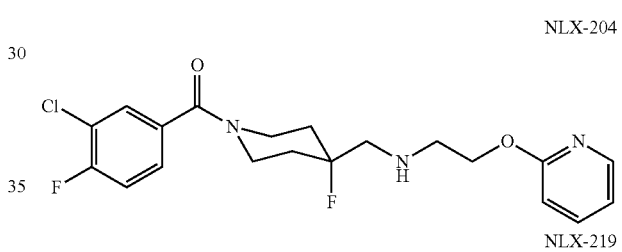

NLX-204

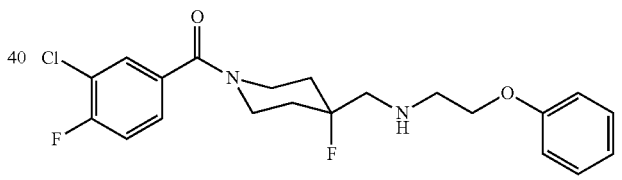

NLX-219

Or one of the pharmaceutically acceptable salts or esters thereof.

The compounds of formula (II), their high selectivity for serotonin 5-HT$_{1A}$ receptors, their biased agonism profile for ERK1/2 phosphorylation and their synthesis are disclosed in Sniecikowska et al. Journal of Medicinal Chemistry, 2019, 62, 2750-2771, PMID 30721053.

According to an embodiment, the compounds may be in the form of their free base, or alternatively, in the form of pharmaceutically acceptable salts such as hydrochloride, oxalate, dihydrochloride, fumarate, maleate, tosylate, salicylate, sulfonate or benzoate.

The identification of those subjects who are in need of treatment of herein-described conditions is well within the ability and knowledge of one skilled in the art. A clinician skilled in the art can readily identify, by the use of clinical tests, physical examination, genetic tests and medical/family history, those subjects who are in need of such treatment. These subjects typically suffer from a disease associated with SUDEP, such as seizures, Fragile X syndrome (FXS), Rett syndrome, Dravet syndrome, Guillain-Barré syndrome, Ohtahara syndrome and Angelman syndrome or diseases associated with the FMR1, SCN1A, SCN1B, SCN8A, SCN2A, GNB5, KCNA1, CDKL5 or DEPDC5 gene dysfunction.

According to an embodiment, patients suffering from a disease associated with SUDEP may exhibit a FMR 1 gene dysfunction.

Actual dosage levels of the compounds may be varied so as to obtain an amount of the active ingredient that is effective to obtain a desired therapeutic response for a particular composition and method of administration. The selected dosage level therefore depends upon the desired therapeutic effect, on the route of administration, on the desired duration of treatment and other factors, e.g., the condition of the patient.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of the compounds which is required to achieve the desired biological effect will vary depending upon a number of factors, including the type of formulation of the drug to be administered, the type of disease, the disease state of the patient and the route of administration.

In general terms, the preferred dosage of a drug to be administered is likely to depend on such variables as the type and extent of progression of the disease or disorder, the overall health status of the particular patient, the relative biological efficacy of the compound selected, and formulation of the compound excipient, and its route of administration.

The daily dose of the selective 5-$HT_{1A}$ receptor agonist may generally be comprised between 0.1 mg/day and 10 mg/day in a human patient, more particularly between 0.5 and 3 mg/day.

According to a further embodiment, the method of the invention also comprises the administration of one or more further active ingredient, typically administered in the treatment or prevention of seizures.

The selective 5-$HT_{1A}$ receptor agonist can be formulated into a pharmaceutical composition by admixture with one or more pharmaceutically acceptable excipients.

The compositions may conveniently be administered in unit dosage form and may be prepared by any of the methods well known in the pharmaceutical art, for example, as described in Remington: The Science and Practice of Pharmacy, 20$^{th}$ ed.; Gennaro, A. R., Ed.; Lippincott Williams & Wilkins: Philadelphia, PA, 2000.

The selective 5-$HT_{1A}$ receptor agonist may be administered by various administration routes such as oral; parenteral including sub-cutaneous, intramuscular, intra-venous; sublingual, topical; local; intratracheal; intranasal; transdermal or rectal, the active ingredients being combined with a pharmaceutically acceptable excipient or vehicle in one or two pharmaceutical compositions.

In particular, the formulations suitable for parenteral administration are sterile and include emulsions, suspensions, aqueous and non-aqueous injection solutions, which may contain suspending agents and thickening agents and anti-oxidants, buffers, bacteriostats and solutes which render the formulation isotonic, and have a suitably adjusted pH, with the blood of the intended recipient. For the topical application, the compositions of the invention may be used as creams, gels, ointments or lotions.

According to the invention, oral administration in an appropriate formulation is advantageously used. Formulations which are suitable to be administered orally to a patient include discrete units such as capsules, such as soft or hard gelatine, tablets, each containing a predetermined amount of selective 5-$HT_{1A}$ receptor agonist. They also include powder; granules; solutions or suspensions in an aqueous liquid or a non-aqueous liquid, or oil-in-water liquid emulsion or water-in-oil liquid emulsion. Gastrointestinal resistant formulations are also contemplated for oral formulations, in particular for duloxetine.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable excipient" includes in particular diluents, adjuvants, carriers, or vehicles. The use of such ingredients for pharmaceutical active substances is well known in the art.

In the context of the invention, the term "treating" or "treatment", as used herein, means reversing, alleviating, inhibiting the progress of, or preventing the disorder or condition to which such term applies, or one or more symptoms of such disorder or condition.

As used herein "prevention" refers to the prophylaxis of a condition and in particular aims at decreasing the risk that said condition occurs or at decreasing the extent to which the condition will occur.

"Therapeutically effective amount" means an amount of a compound/pharmaceutical composition according to the present invention effective in producing the desired therapeutic effect.

According to the invention, the term "patient", or "patient in need thereof" is intended for a human or non-human mammal affected or likely to be affected with the above disorders. Preferably, the patient is a human.

The compounds may be administered in unit dosage forms, wherein the term "unit dose" means a single dose which is capable of being administered to a patient, and which can be readily handled and packaged, remaining as a physically and chemically stable unit dose comprising either the active compound itself, or as one or two pharmaceutically acceptable compositions.

The appropriate unitary dosage forms comprise the oral forms; the sublingual, buccal, intratracheal, intraocular, intranasal forms, by inhalation, the topical, transdermal, sub-cutaneous, intramuscular or intra-venous, and the rectal forms and the implants.

It should be noted that the alternative embodiments expressed hereabove are not mutually exclusive and may be considered in addition to each other.

BRIEF DESCRIPTION OF THE DRAWINGS

The invention will be described in connection with the attached drawings.

Figure 1:
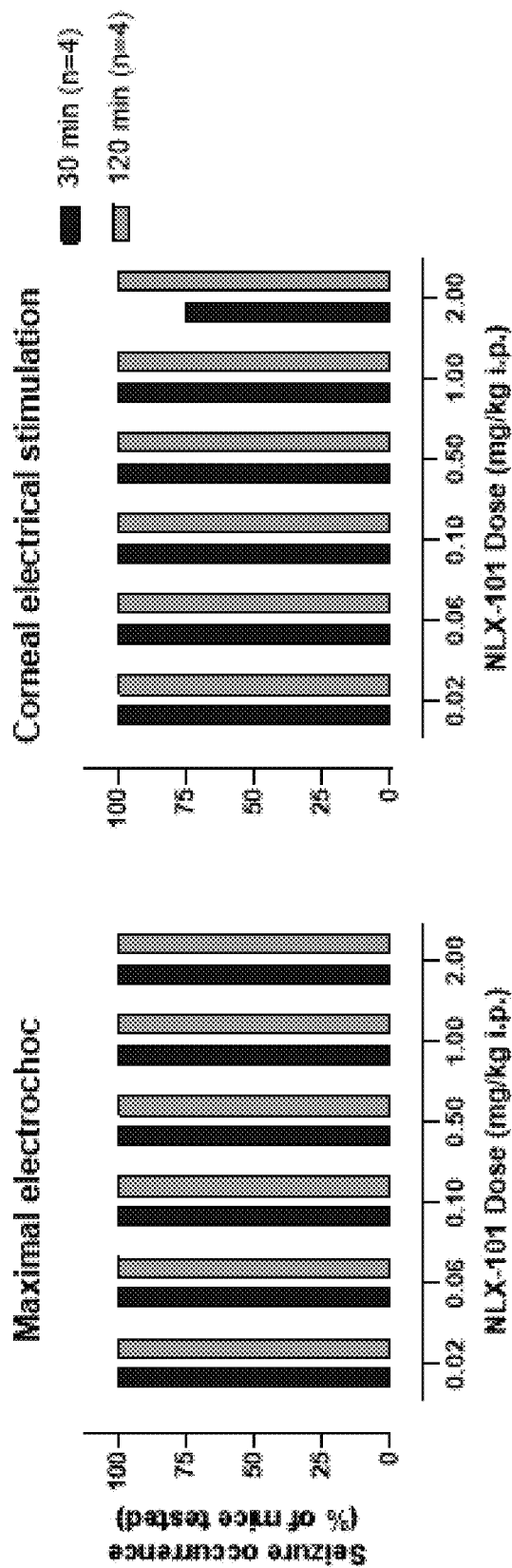
FIG. 1 illustrates the lack of anti-seizure activity of NLX-101 in two models of seizures in wild-type mice.

The invention will be further understood by reference to the following illustrative examples:

EXAMPLES

Methods

Seizures Induced by Corneal Electrical Stimulation (CES) in Wild-Type Mice

Experiments were carried out in accordance with the National Institute of Neurological Disorders and Stroke (NINDS) Epilepsy Therapy Screening Program (https://panache.ninds.nih.gov/TestDescription/Test6HZ). The CES test was carried out using wild-type male CF-1 mice. Seizures were induced by a low frequency (6 Hz, 0.2 msec rectangular pulse), long-duration (3 sec), 44 mA current (double the current producing seizures in 97% of animals) delivered through corneal electrodes (Barton M E, Klein B D, Wolf H H, White H S. Pharmacological characterization of the 6 Hz psychomotor seizure model of partial epilepsy. Epilepsy Res. 2001; 47:217-27). A drop of 0.5% tetracaine hydrochloride in 0.9% saline (anesthetic/electrolyte) solution was applied to the eyes just prior to the placement of corneal electrodes. The seizure in mice is characterized by an initial momentary stun followed immediately by jaw clonus, forelimb clonus, twitching of the vibrissae, and "Straub tail". Animals not displaying this behavior within the one-minute observation period are considered "protected" from seizures.

Testing for anti-seizure activity in the CES model was performed with 4 male mice/dose/time point. Six doses of NLX-101 (0.02, 0.06, 0.5, 1 and 2 mg/kg i.p.) and two timepoints (30 and 120 min after drug administration) were tested.

Seizures Induced in the Maximal Electroshock Seizure (MES) Test

Experiments were carried out in accordance with the National Institute of Neurological Disorders and Stroke (NINDS) Epilepsy Therapy Screening Program (https://panache.ninds.nih.gov/TestDescription/TestMES). The MES test was carried out using wild-type male mice. MES is a model for generalized tonic-clonic seizures and provides an indication of a compound's ability to prevent seizure spread when all neuronal circuits in the brain are maximally active (White H S, Johnson M, Wolf H H, Kupferberg H J. The early identification of anticonvulsant activity: role of the maximal electroshock and subcutaneous pentylenetetrazol seizure models. Ital J Neurol sci. 1995; 16:73-7). These seizures are highly reproducible and are electrophysiologically consistent with human seizures. Seizures were induced by a high frequency (60 Hz) of alternating current at 50 mA over a short duration (0.2 sec) delivered through corneal electrodes. Prior to stimulation, corneas were irrigated with 0.5% tetracaine hydrochloride for local anesthesia and 0.9% saline to improve electrical conductivity. Seizures induced by MES are characterized by tonic extension of forelimbs and hindlimbs that is followed by brief episodes of clonic activity of the forelimbs and hindlimbs. An animal is considered "protected" from MES-induced seizures upon abolition of the hindlimb tonic extensor component of the seizure. Testing for anti-seizure activity in the MES model was performed with 4 male mice/dose/time point. Six doses of NLX-101 (0.02, 0.06, 0.5, 1 and 2 mg/kg i.p.) and two timepoints (30 and 120 min after drug administration) were tested.

Audiogenic Tonic-Clonic Seizures (TCS) in FMR1 Transgenic Mice

FMR1 knock-out (KO) mice were bred and weaned at postnatal day 21 (P21), and all mice were tested between P21 to P23. NLX-101 was administered at doses of 0.6, 1.2, 1.8 and 2.4 mg/kg i.p. Control FMR1 KO mice received saline. NLX-101 or saline was injected 10 min before subjecting the mice to the auditory stimulus.

To differentiate each mouse for post-hoc video analysis, mice were color coded prior to drug or saline administration. Mice (up to 4/cage) were then put in a cage with a lid; after 10 min, a speaker was placed on top of the lid, and the cage placed in a sound attenuation booth (Gretch-Ken Inc., OR); the auditory stimulus was a continuously alternating up and down frequency modulated sweep with frequencies between 2-8 kHz, presented at an intensity between 105-110 dB for 15 min. The procedure lasted a total of 20 min starting with 5 min of habituation (without a sound stimulus). The full 20-min procedure was video recorded for off-line analysis.

The typical behavior of FMR1 knock-out mice subjected to loud audio stimulus includes tonic-clonic seizures (TCS: the mouse lays on the cage bottom with hindlimb extension), and death by respiratory arrest (manifested by a deep respiratory gasp and relaxation of pinna).

The latency time (from the stimulus onset) to the occurrence of TCS and death were recorded with a stopwatch (precision: 1 sec). Survival analysis was used to analyze the probability of TCS or death by log-rank test.

Figure 2:
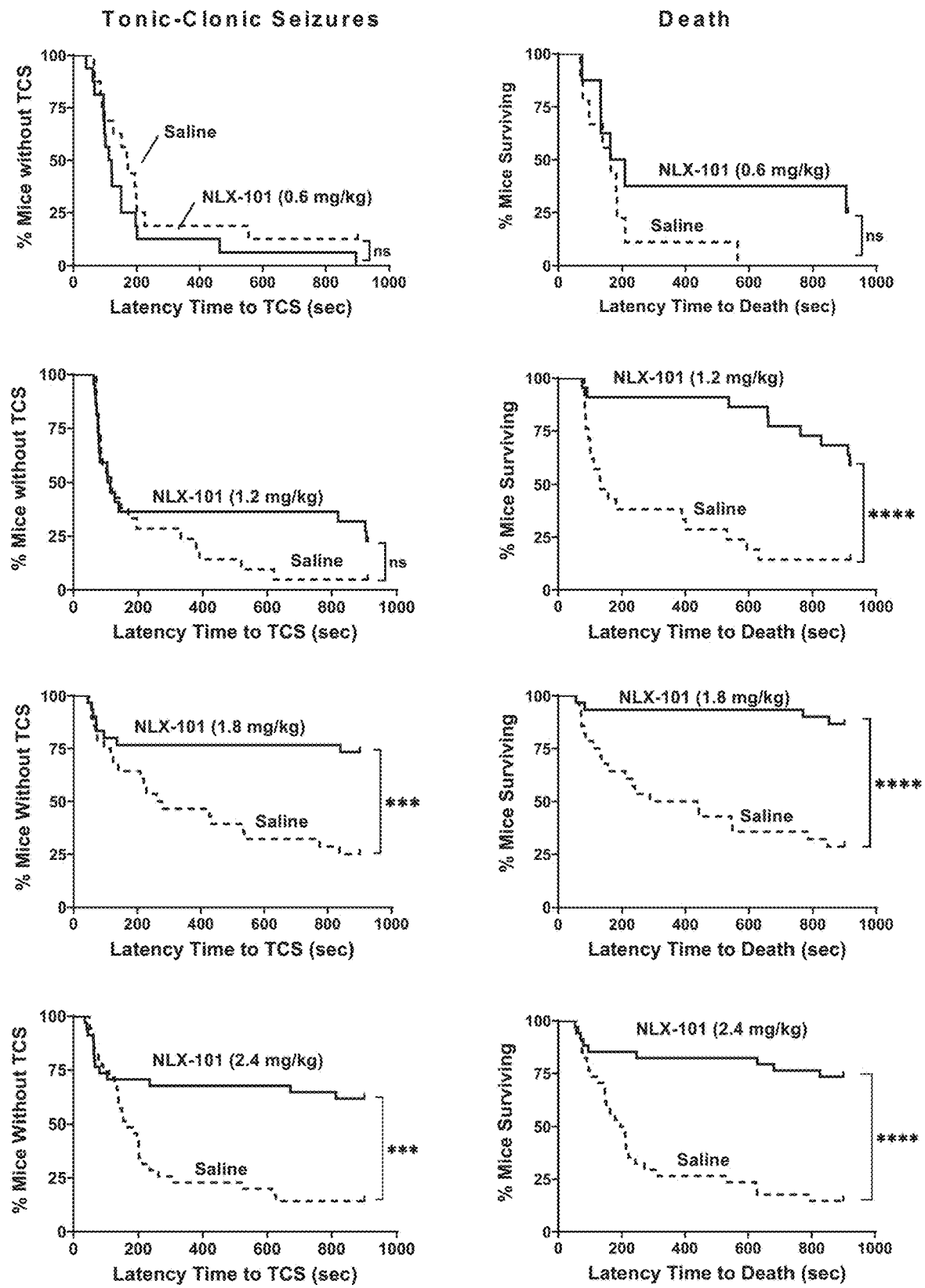
FIG. 2 illustrates the dose-dependent reduction by NLX-101 of tonic-clonic seizures (TCS) and death rate in FMR 1 transgenic mice (ns: not significant;*p<0.001, **p<0.0001, Log-rank (Mantel-Cox) test).

The results are illustrated in FIGS. 1 and 2:

In wild-type mice, NLX-101, over a wide range of doses (0.02 to 2 mg/kg i.p.) and at 30- and 120-min post-injection, did not affect the occurrence of seizures in the maximal electroshock seizures (MES) test (left panel). In the corneal electrical stimulation (CES) seizure test (right panel), NLX-101 reduced seizure occurrence in only 1 out of 4 mice at the highest dose tested, and at only one time point (30 min post injection). The minimal activity of NLX-101 in the MES and CES tests suggest that it does not possess anti-seizure activity (FIG. 1).

In contrast, NLX-101 dose-dependently reduced the percentage of FMR1 knock-out mice displaying tonic-clonic seizures, with significant effects at 1.8 and 2.4 mg/kg (left panels). NLX-101 also dose-dependently reduced the number of FMR1 knock-out mice that died, with significant effects at doses of 1.2, 1.8 and 2.4 mg/kg (right panels). Each experimental groups consisted of 14 or 16 mice (half of which were males, half were females). These data indicate that NLX-101 displays robust anti-seizure and anti-SUDEP activity in FMR1 knock-out mice (FIG. 2).

The invention claimed is:

1. A method of treatment of seizures in a patient exhibiting a FMR1 gene dysfunction and suffering from a disease with which Sudden Unexpected Death in Epilepsy (SUDEP) occurs, the method comprising administering a therapeutically effective amount of NLX-101 (also known as F-15599) having formula (IA):

(IA)

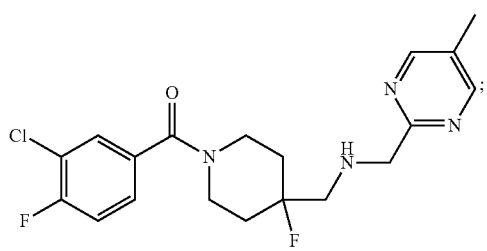

or
a pharmaceutically acceptable salt thereof.

2. The method of claim 1, wherein said disease with which SUDEP occurs is Fragile X syndrome.

3. A method of treating Fragile X syndrome in a patient exhibiting a FMR1 gene dysfunction, the method comprising administering to the patient a therapeutically effective amount of NLX-101 (also known as F-15599) having formula (IA):

(IA)

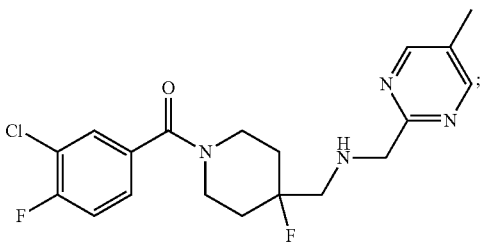

or
a pharmaceutically acceptable salt thereof.

* * * * *